(12) United States Patent
Yokoyama et al.

(10) Patent No.: US 6,407,404 B1
(45) Date of Patent: Jun. 18, 2002

(54) APPARATUS FOR THE EXAMINING DEFECT OF MONOLITHIC SUBSTRATE AND METHOD FOR EXAMINING THE SAME

(75) Inventors: Yoshio Yokoyama, Anjo; Shigeru Kawamura, Kariya, both of (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/526,065

(22) Filed: Mar. 15, 2000

(30) Foreign Application Priority Data

Mar. 15, 1999  (JP) .......................................... 11-068868

(51) Int. Cl.⁷ ............................................. G01N 21/88
(52) U.S. Cl. .............................. 250/559.46; 250/559.4; 250/559.45; 250/208.1
(58) Field of Search .................... 250/559.46, 559.4, 250/559.45, 208.1, 559.36; 356/237.2, 237.3, 237.4, 237.5

(56) References Cited

U.S. PATENT DOCUMENTS 4,330,775 A * 5/1982 Iwamoto et al. ...... 340/146.3 P
6,021,214 A * 2/2000 Evans et al. ................. 382/141

FOREIGN PATENT DOCUMENTS

| JP | 60-214209 | 10/1985 |
| JP | 2-210208 | 8/1990 |
| JP | 3-93708 | 9/1991 |
| JP | 6-242013 | 9/1994 |
| JP | 7-270335 | 10/1995 |
| JP | 7-280537 | 10/1995 |

* cited by examiner

Primary Examiner—Robert H. Kim
Assistant Examiner—Courtney Thomas
(74) Attorney, Agent, or Firm—Law Offices of David G. Posz

(57) ABSTRACT

An apparatus inputs an image of a regularly latticed-patterns. The inputted image data is transformed into frequency data by the Fourier transformation. The frequency data is restored into image data after it is processed. The processing of the frequency data includes a process for removing a frequency component corresponding to the latticed patterns. The processing of the frequency data further includes a process for removing a frequency component corresponding to a shape of an area of the latticed patterns. The processed data is used for detecting and examining a defect. It is possible to examine a defect accurately.

16 Claims, 11 Drawing Sheets

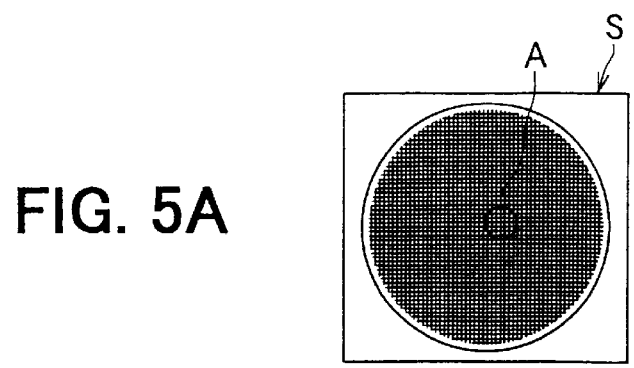
FIG. 5A
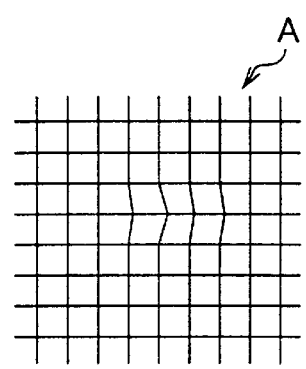
FIG. 5B
FIG. 6
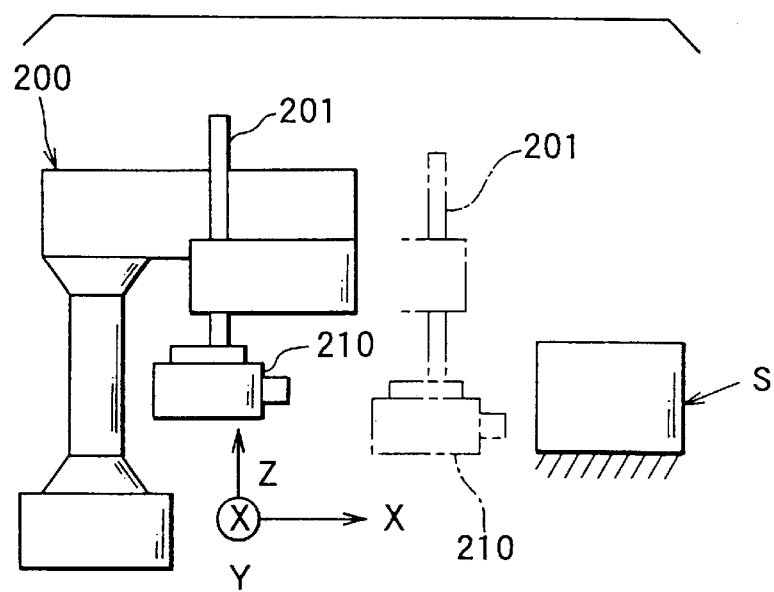

APPARATUS FOR THE EXAMINING DEFECT OF MONOLITHIC SUBSTRATE AND METHOD FOR EXAMINING THE SAME

CROSS-REFERENCE TO RELATED APPLICATION

This application is based on Japanese Patent Application No. 11-68868 filed on Mar. 15, 1999, the contents of which are incorporated herein by reference.

BACKGROUND OF THE INVENTION

1. Field of the Invention

The present invention relates to an apparatus for examining a defect of a regularly disposed lattice patterns of a monolithic substrate and a method for examining the same.

2. Description of Related Art

Conventionally, for instance, the following method is known in this kind of an examining method. The examining method comprises capturing latticed patterns of a monolithic substrate, determining each of patterns from a captured image, and evaluating a shape of the determined pattern.

Incidentally, in a case of a monolithic substrate which has a lot of numbers of regularly disposed patterns, a higher magnification image is required for maintaining a measuring accuracy of a shape of the pattern sufficiently. Therefore, a lot of input processes of images are required because a field of a camera must be narrowed. As a result, there are disadvantages that the prior art brings an enlargement of a memory and an extension of a processing time.

A defect examining apparatus for addressing the above-mentioned problems is proposed in JP-A-6-242013. The apparatus captures an image of a wide area of an object having regularly repeated patterns, and processes image data which is captured. In this prior art, the image data is transformed into space frequency data by the Fourier transformation. A range of the space frequency data corresponding to the repetition of the patterns is masked. The masked space frequency data is processed by the Fourier reverse transformation to restore image data. The restored image data is provided for examining the defect of the repeated patterns. As a result, a ratio of a component corresponding to an irregularly formed defect to the masked data is increased relatively. The defect is indicated in an emphasized manner in the restored image data. Therefore, it is possible to detect the defect easily.

SUMMARY OF THE INVENTION

However, the following problems are appeared when the above-described method is applied for a monolithic substrate.

Specifically, the monolithic substrate has latticed patterns as repeated patterns which reach to an outer edge. The outer edge terminates the latticed patterns. Therefore, a defect can't be sufficiently emphasized because an influence of an outer shape of the monolithic substrate remains, even if frequency components corresponding to regularly latticed patterns are removed. Therefore, it is difficult to accurately examine the defect based on the restored image data.

It is a further object of the present invention to provide a method and an apparatus to accurately examine a particular defect of the monolithic substrate of the lattice.

According to a first aspect of the present invention, captured image is processed by the Fourier transformation. Data corresponding to a particular component of frequency is removed from frequency data obtained by the Fourier transformation. The particular component includes a first component which is a frequency component depending on a regularity of the latticed patterns of the monolithic substrate. For instance, the first component is obtained on the basis of a perfect latticed-patterns having no defect. The particular component further includes a second component depending on an outer shape where the latticed patterns are terminated. For instance, a circle corresponding to an end shape of the monolithic substrate obtains the second component. As a result, it is obtained that data in which the particular components are declined. The data is processed by the Fourier reverse transformation. After that, the defect is detected based on the data after transformed by the Fourier reverse transformation. For instance, frequency data corresponding to a predetermined range is removed. The range is extended from a center which is the component corresponding to the regularly latticed-patterns. In the present invention, mean value of the image data is calculated at each lattice. The defect can be indicated when the mean value is out of a predetermined range.

Further, areas of applicability of the present invention will become apparent from the detailed description provided hereinafter. It should be understood that the detailed description and specific examples, while indicating preferred embodiments of the invention, are intended for purposes of illustration only, since various changes and modifications within the spirit and scope of the invention will become apparent to those skilled in the art from this detailed description.

BRIEF DESCRIPTION OF THE DRAWINGS

The present invention will become more fully understood from the detailed description and the accompanying drawings, wherein:

FIG. 5A is a view showing a captured image;

FIG. 5B is a enlarged view of an area A which is proposed for a defect in FIG. 5A;

FIG. 6 is a schematic view of the second embodiment;

DETAILED DESCRIPTION OF PRESENTLY PREFERRED EXEMPLARY EMBODIMENTS

Figure 1:
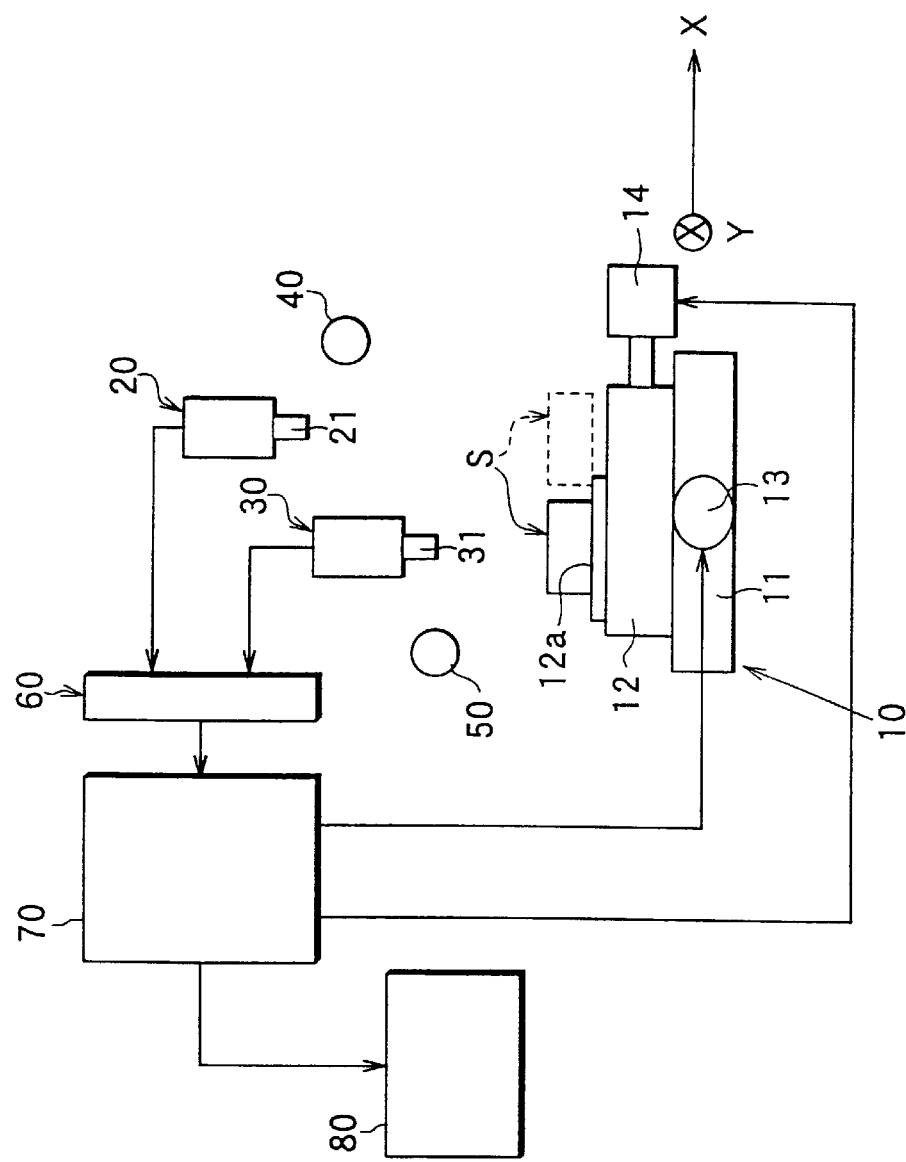
FIG. 1 is a schematic view of a first embodiment of the present invention.

Preferred embodiments of the present invention are described hereinafter with reference to the accompanying drawings. Hereafter, an embodiment of the present invention will be described based on FIG. 1 through FIG. 5. FIG. 1 shows an embodiment of an image pick up type examining apparatus. The examining apparatus has a XY-table 10. The XY-table 10 has a X-table 11, a Y-table 12 and motors 13, 14 for driving the tables respectively. The X-table 11 is driven by the motor 13 and constructed to move along the X-axis (a direction along right and left in FIG. 1) with the Y-table. The Y-table 12 is driven by the motor 14 and constructed to move along the Y-axis (a vertical direction of a paper of FIG. 1) on the X-table.

A mounting plate 12a is supported on the Y-table 12. An object S to be examined (in this embodiment, the object is a monolithic substrate) is mounted on the mounting plate 12a. Here, latticed patterns (shown in FIG. 5) are formed on a surface of the object S to be examined. The latticed patterns form perfect lattices when the deformation is not formed.

The examining apparatus has a low magnification camera 20 and a high magnification camera 30. Referring to FIG. 1, the low magnification camera 20 supported above the Y-table 12 to orient a receiver 21 toward a right side of the Y-table 12. The low magnification camera 20 captures the surface of the object S under a lighting of a light 40, and outputs captured data. In this embodiment, a field of the low magnification camera 20 is about 100 mm×100 mm. The high magnification camera 30 is supported above the Y-table 12 to orient a receiver 31 toward a left side of the Y-table 12. The high magnification camera 30 captures the surface of the object S under a lighting of a light 50, and outputs captured data. In this embodiment, a field of the high magnification camera 30 is about 7 mm×7 mm. The light 40 is supported on a position shown in FIG. 1 so that the light 40 lights up the object S from right side of the low magnification camera 20. The light 50 is supported on a position shown in FIG. 1 so that the light 50 lights up the object S from left side of the high magnification camera 30. Lighting areas of the lights 40 and 50 are not overlapped on the surface of the object S each other. An A-D converter 60 converts image data of the low magnification camera 20 and the high magnification camera 30 into low magnification image data and high magnification image data, respectively, and outputs them to a microcomputer 70.

Figure 2:
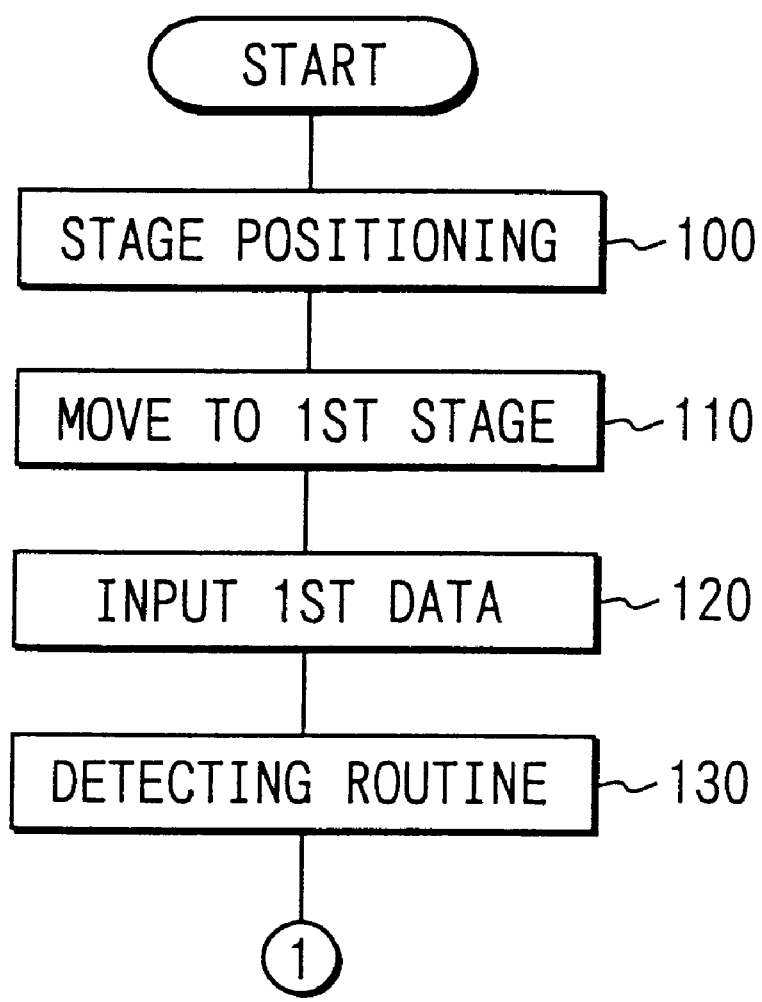
FIG. 2 is a first half of a flowchart of the first embodiment.
Figure 3:
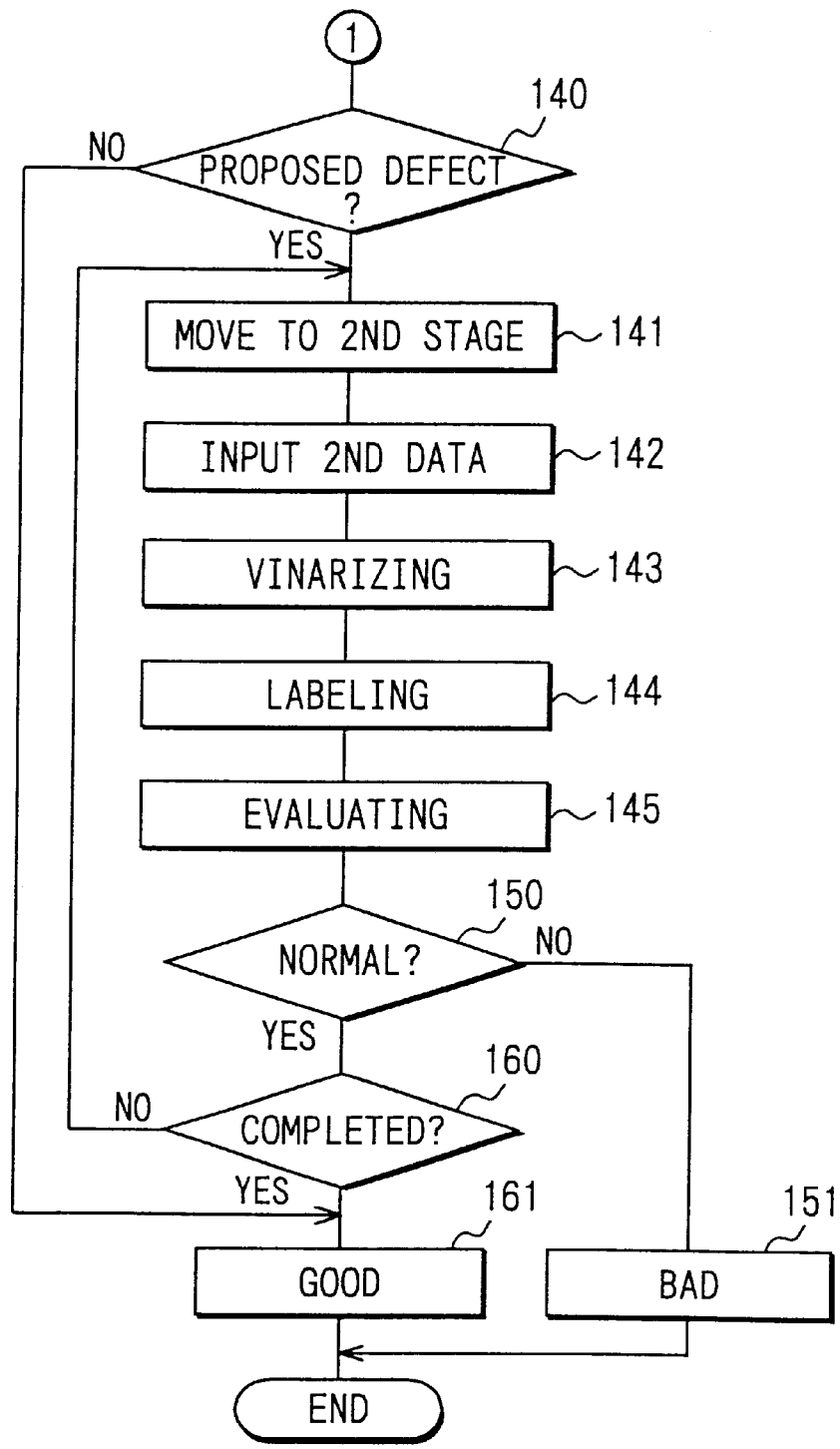
FIG. 3 is a second half of a flowchart of the first embodiment.
Figure 4:
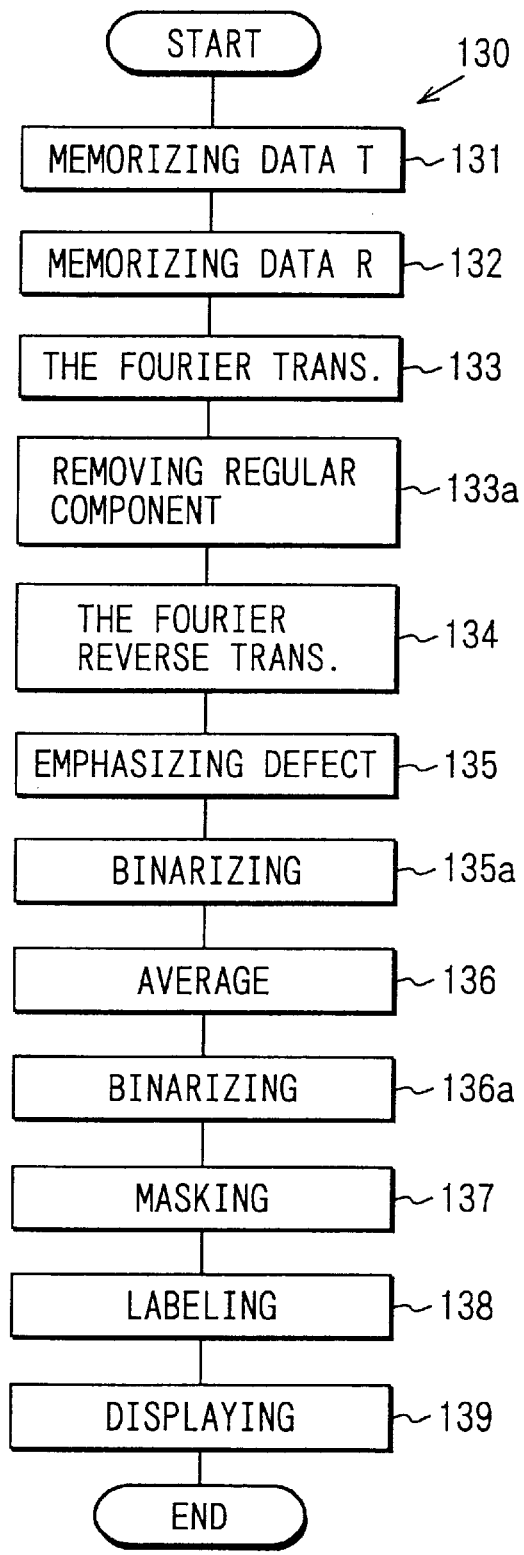
FIG. 4 is a flowchart of the routine 130.

The microcomputer 70 executes a program by following the flowcharts shown in FIG. 2 through FIG. 4. The microcomputer 70 processes a defect examining of the surface on the object S and a display control of a CRT 80. The microcomputer 70 memorizes the program in a memory.

In the above-constructed embodiment, the microcomputer 70 begins to execute the program shown in FIG. 2 and FIG. 3, at first, step 100 of FIG. 2 is executed. At step 100, a stage positioning process of the XY-table 10 is executed. For instance, the motors 13 and 14 drives the X-table 11 and the Y-table 12 respectively so that the object S can be mounted on the mounting plate 12a. After that, the object S is mounted on the mounting plate 12a as shown in FIG. 1. The surface to be examined should be faced upwardly.

After that, at step 110, the XY-table 10 is driven to a low magnification station for an examining process. That is, the motor 13 and 14 drives the X-table 11 and the Y-table 12 to a position (referred to as a low magnification station or a first station) where the surface of the object S is located within the field of the low magnification camera 20. Therefore, the object S is positioned on the low magnification station. After that, the low magnification camera 20 captures an image of the surface of the object S at low magnification when the light 40 lights up the surface of the object S. The low magnification camera 20 outputs captured data to the A-D converter 60. The A-D converter 60 converts the captured data from the low magnification camera 20 digitally and outputs it to the microcomputer 70 as low magnification captured data. At step 120, the microcomputer 70 inputs the low magnification captured data (first data).

After that, a defect detecting routine 130 is executed (shown in FIG. 4). In the defect detecting routine 130, at step 131, the microcomputer 70 temporally stores the low magnification image data into a RAM as a memory data T.

Next, at step 132, a circular area in which the latticed patterns of the monolithic substrate are formed is exclusively picked up as an area except for an outer edge of the monolithic substrate. The area is memorized in the RAM as area data R. At step 133, the memorized data T is processed by the two-dimensional Fourier transformation. The processed data, which indicates frequency components, is temporally memorized in the RAM as memorized data Tf. Here, in a case that image data of the monolithic substrate is processed by the two-dimensional Fourier transformation, the processed data contains a frequency component corresponding to the latticed patterns as the repeated patterns and a frequency component corresponding to the outer edge (circular shape) of the monolithic substrate terminating the repeated patterns. Therefore, a defect signal indicating the defect of the latticed patterns is not emphasized sufficiently by declining the frequency component corresponding to the latticed patterns, because the frequency component corresponding to the outer edge of the monolithic substrate is not removed. In this embodiment, it is designed to emphasize the defect signal and to improve an examining accuracy of the defect by declining not only the frequency component corresponding to the latticed patterns but also the frequency component corresponding to the outer edge of the monolithic substrate. For instance, a circular range having a center corresponding to the frequency component of the latticed patterns and having a predetermined area is masked and removed from the memorized data Tf. Therefore, it is possible to decline both the frequency component of the latticed patterns and the frequency component of the outer shape from the memorized data Tf sufficiently. Hereafter, the process will be described in detail.

Figure 9A:
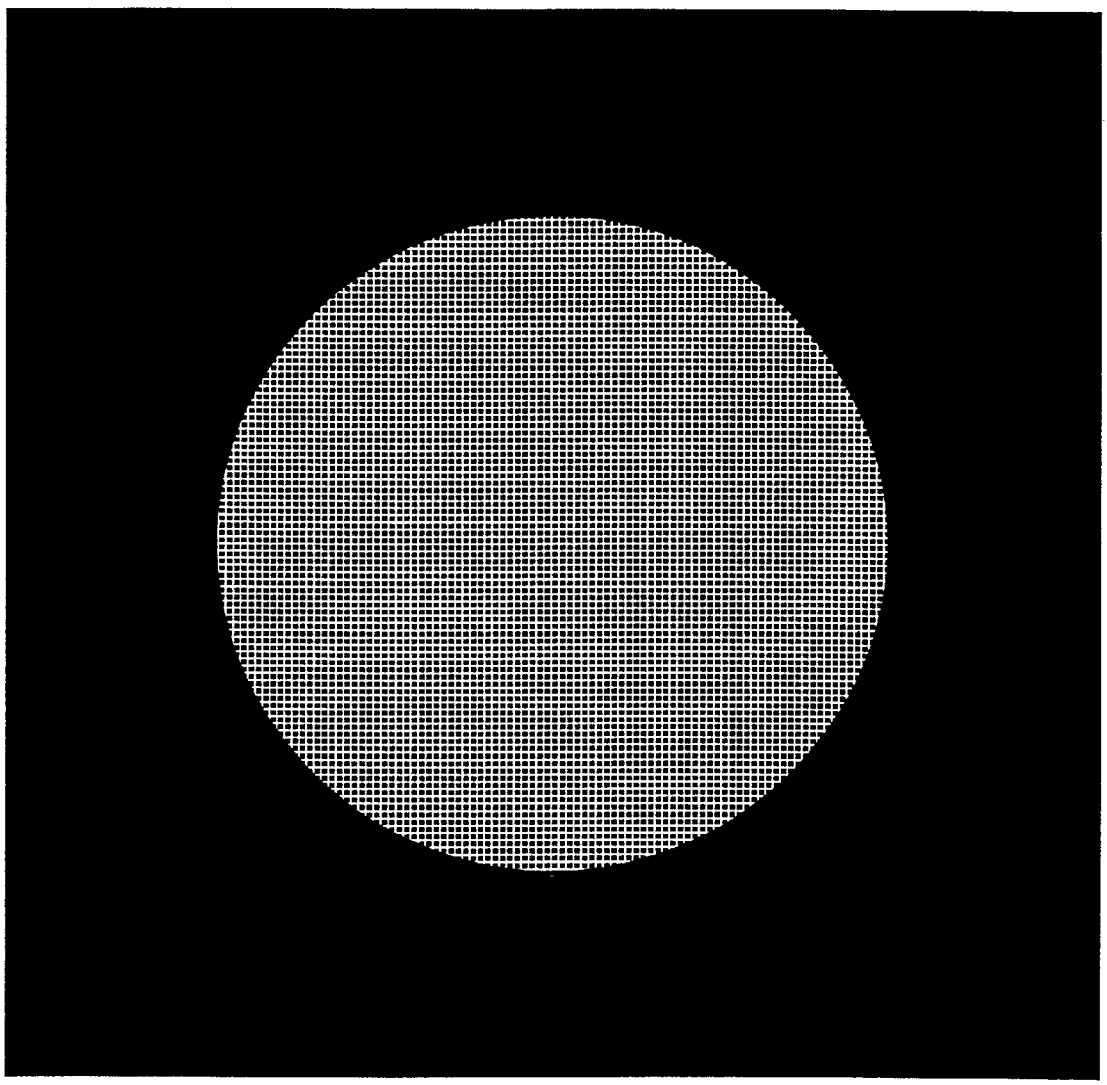
FIG. 9A is a view showing an image before the Fourier transformation.

The image f (referred to FIG. 9A) of the monolithic substrate can be indicated as a product of a repeated patterns signal g and an outer shape pattern signal h having no repetition.

f=g·h

The Fourier transformed map of the f, g and h is represented by a F, G and H respectively, the F can be represented by a convolution of the G and the H.

F=G*H

Figure 7A:
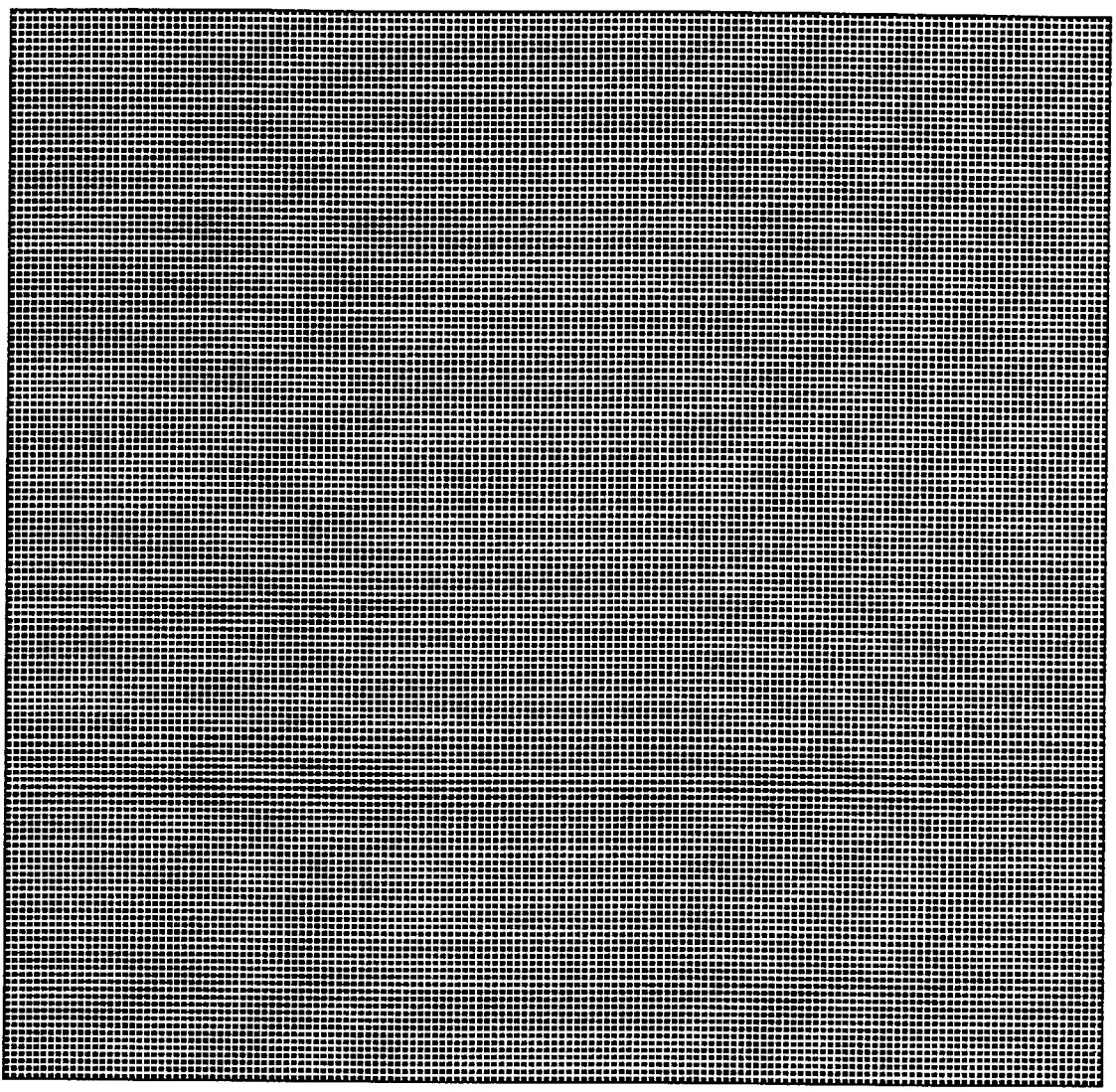
FIG. 7A is a view showing an image before the Fourier transformation.
Figure 7B:
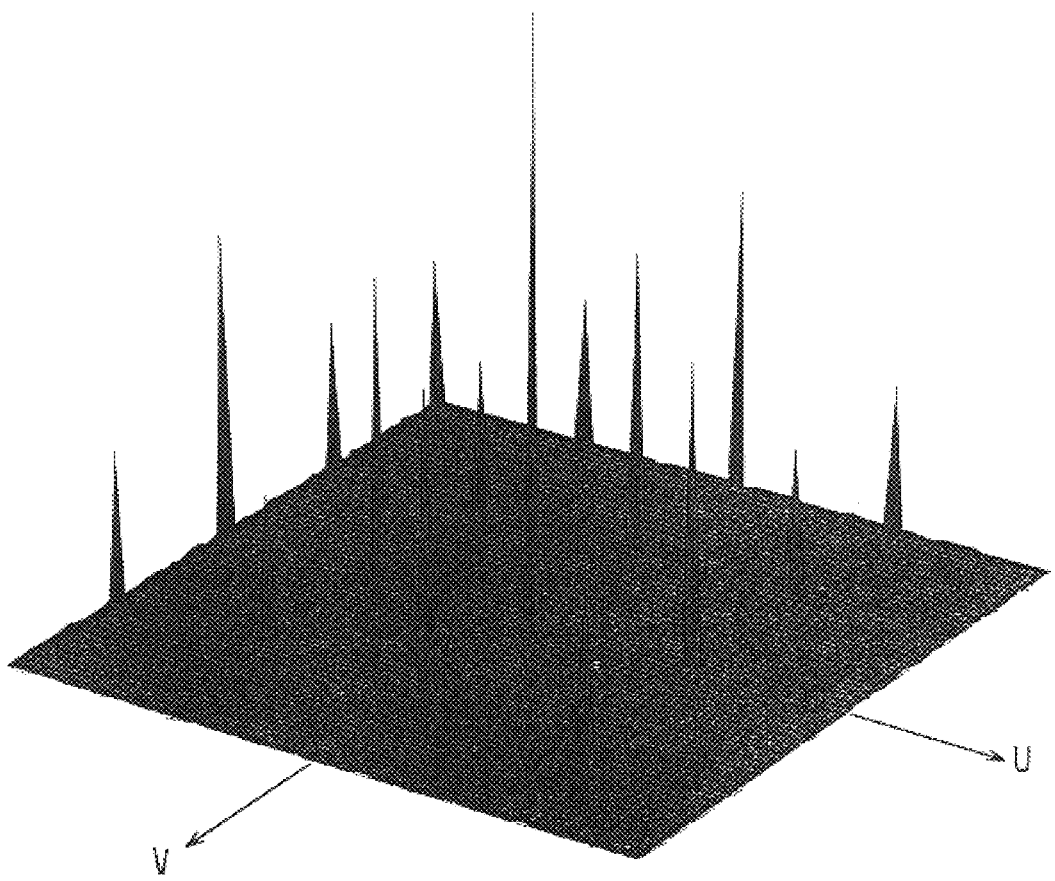
FIG. 7B is a graph showing a result of the Fourier transformation of the image in FIG. 7A.

Here, in a case that the latticed patterns of the monolithic substrate shown in FIG. 7A are captured as a digital image signal and that is processed by the two-dimensional Fourier transformation, a Fourier transformed map is shown in FIG. 7B. That is, the Fourier transformed map G of the repeated patterns signal g generated by the latticed patterns indicates a power spectrum having a discrete impulses at the frequencies corresponding to the repeated patterns. Therefore, if there is no influence of the outer shape pattern signal h, it is possible to decline the frequency component corresponding to the repeated patterns sufficiently by removing and masking only the frequency component corresponding to the repeated patterns. In this case, the masking is only performed on a small range of a frequency space, therefore an irregular frequency component corresponding to the defect of the repeated patterns is hardly removed. Accordingly, the defect of the latticed patterns is restored on the image data finely by applying the Fourier reverse transformation only to the frequency data after the frequency component corresponding to the repeated patterns is masked. However, the frequency data of the image data of the monolithic substrate processed by the Fourier transformation includes the influence of the outer edge pattern signal h. Therefore, it is impossible to emphasize the defect of the latticed patterns, if only the frequency component corresponding to the repeated patterns is merely removed.

Figure 8A:
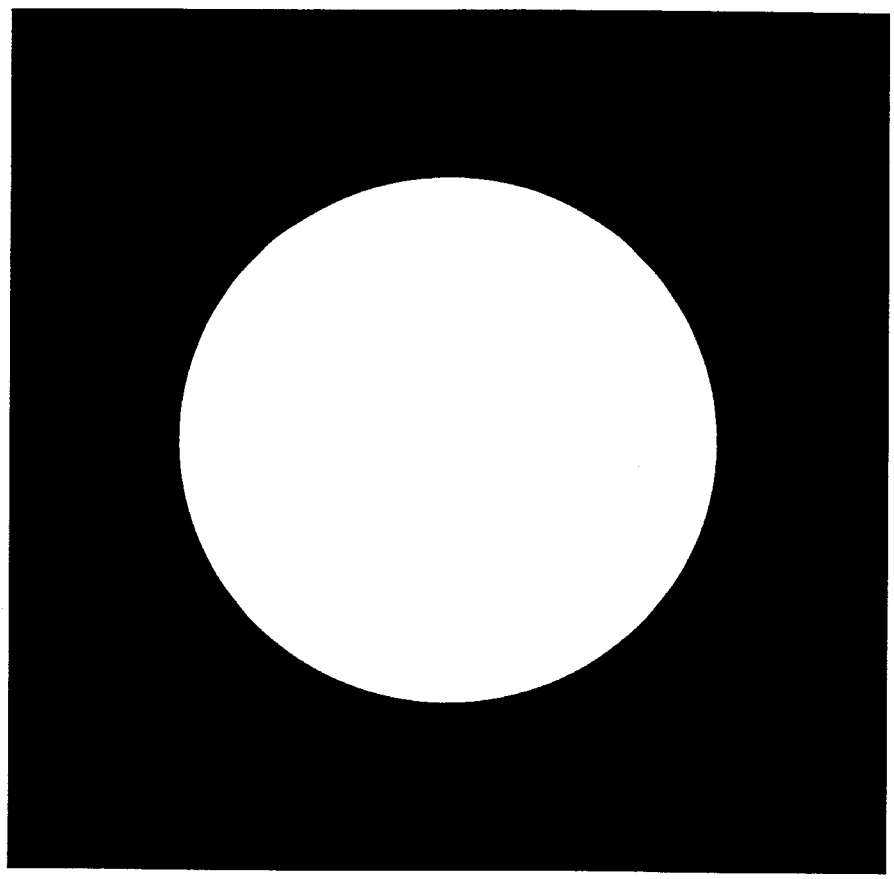
FIG. 8A is a view showing an image before the Fourier transformation.
Figure 8B:
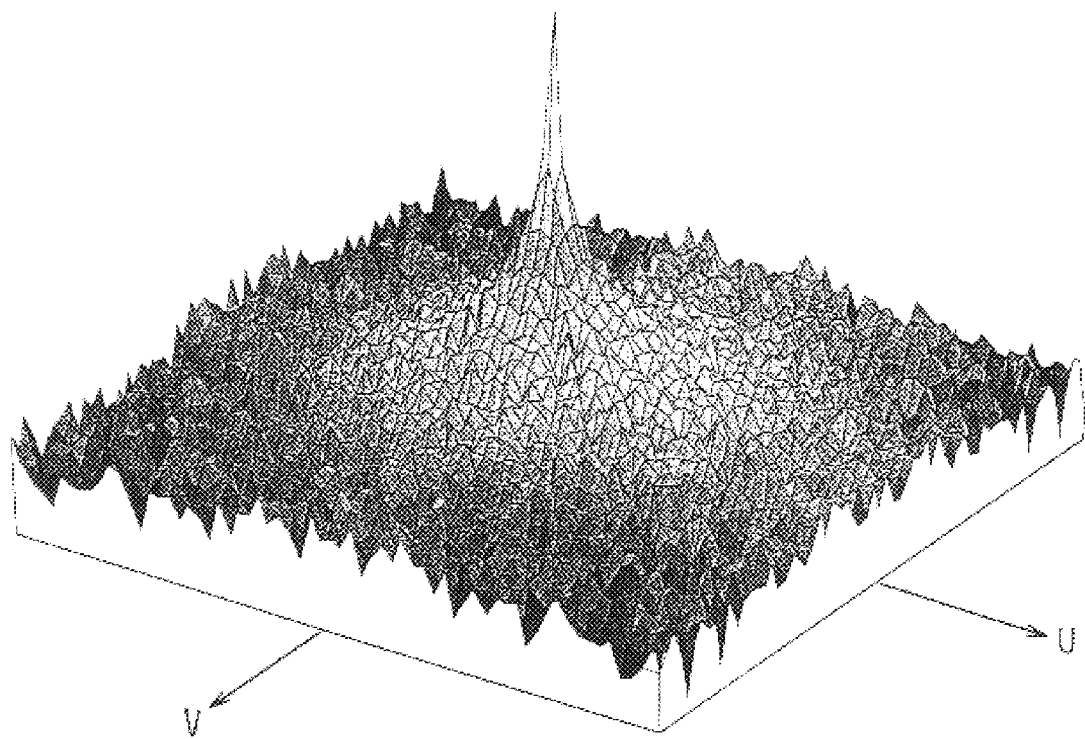
FIG. 8B is a graph showing a result of the Fourier transformation of the image in FIG. 8A.

FIG. 8A shows an image corresponding to the outer edge (circular shape) of the monolithic substrate. FIG. 8B shows a Fourier transformed map when the image of FIG. 8A is transformed. As shown in FIG. 8B, the Fourier transformed map H of the outer shape pattern signal h has a peak at a low frequency component on the frequency space and has a range expanded from the peak as a cone. FIG. 8B shows that a frequency of the peak is zero, and a direct current component is the strongest.

Figure 9B:
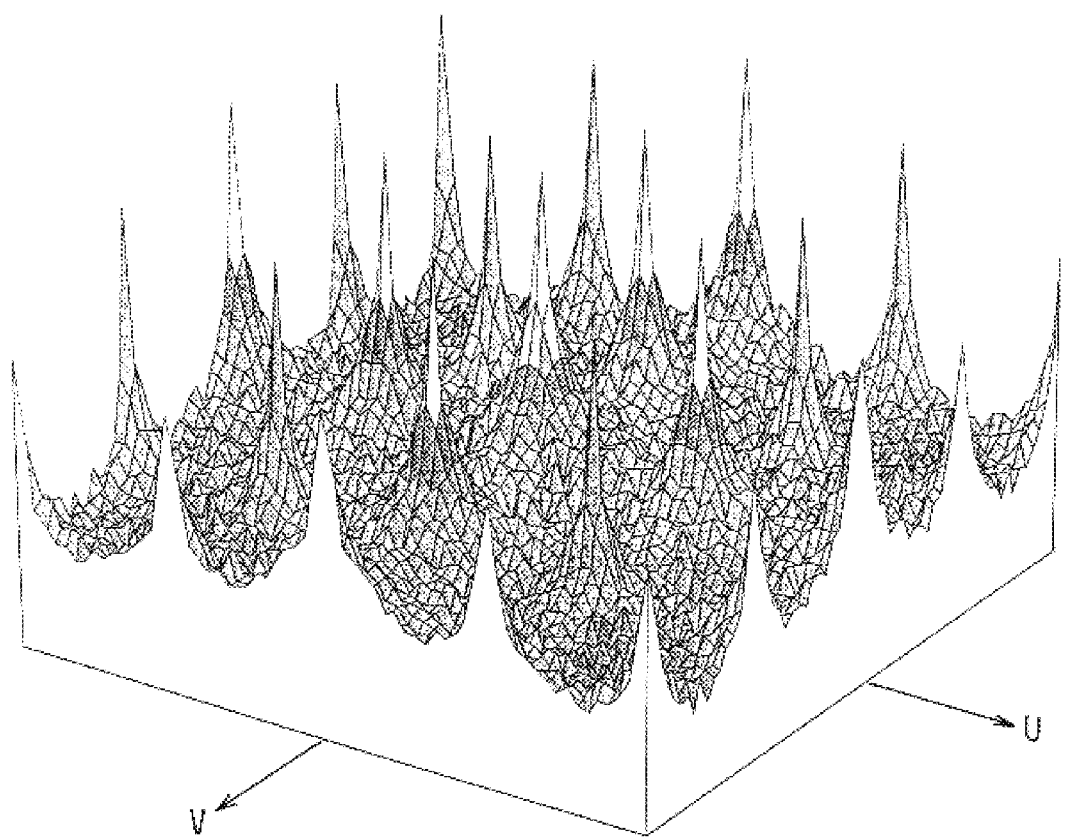
FIG. 9B is a graph showing a result of the Fourier transformation of the image in FIG. 9A.

As described above, the Fourier transformed map F of the image of the monolithic substrate is represented by the convolution of the Fourier transformed map G of the repeated patterns signal g and the Fourier transformed map H of the outer shape pattern signal h. As shown in FIG. 9B, the Fourier transformed map F will be a superposition of the impulses of the Fourier transformed map G and the cone-shape of the Fourier transformed map H.

Then, at step 133a, a removing process of a regular component is executed. It is designed to remove not only the frequency range corresponding to the impulses on the power spectrum of the Fourier transformed map G but also the cone-shaped component of the Fourier transformed map H overlapped on the impulses. Data corresponding to circular ranges are masked and removed. Each range has a center corresponding to the frequency component of the impulse of the power spectrum and has a predetermined area. Therefore, the low frequency component of the Fourier transformed map H is removed from the frequency data. Here, the frequency data still contains a high frequency component of the Fourier transformed map H. The high frequency component corresponds to the outer edge of the monolithic substrate. Accordingly, in a case of the Fourier reverse transformation of the frequency data containing the high frequency component, an influence of the high frequency component is very small relative to the image data within the area. The area is enclosed by the outer edge and the latticed patterns are formed therein. In other words, on the image data restored by the Fourier reverse transformation, the high frequency component only influences a vicinity of the outer edge. Here, the monolithic substrate has patterns, which are not shaped as a square at the vicinity of the outer edge. For example, these patterns will be masked to prevent a flow of exhaust gas, when the monolithic substrate is installed into an exhaust pipe as a catalyst for purifying an exhaust of an engine. Therefore, it is not required to examine a defect on the vicinity of the outer edge. Therefore, the high frequency component contained in the frequency data of the Fourier transformed map H does not prevent the detection of the defect.

At step 134, the memorized data Tf in which the regularity component is removed by the process at step 133 is processed by the two-dimensional Fourier reverse transformation. Next, at step 135, the image data restored by the two-dimensional Fourier reverse transformation is processed to emphasize the defect. In this embodiment, the cone-shaped component of the Fourier transformed map H overlapped with the impulses of the Fourier transformed map G is masked and removed. Therefore, the influence of the outer shape of the monolithic substrate is removed. However, the defect signal is also decreased in the restored image data, because this process masks a lot of ranges of the frequency space. A ratio of S/N is not sufficient for detecting a position of a proposed defect from the restored image data. Therefore, it is preferable to emphasize the defect signal corresponding to the defect portion.

Here, the restored image data is examined. It becomes clear that a high frequency noise is restored at a portion where a normal latticed patterns is formed. It also becomes clear that amplitude of a high frequency noise is increased by the frequency component of the defect signal at a portion where the defect exists. Therefore, a local variance process is carried out for emphasizing an increase of the amplitude as a defect emphasizing process. The local variance process includes a step for dividing the image data into a plurality of local areas, a step for obtaining a signal variance at each of the local areas and a step for increasing the signal amplitude of the local area where the variance is relatively large.

After that, at step 135a, the data, which is processed to emphasize the defect in step 135, is binarized using a predetermined value and whether the amplitude is larger than the predetermined value or not. The binary data replaces the memorized data Tf, and is temporally memorized in the RAM.

At step 136, a local averaging process is applied to the memorized data T of step 131. For instance, an average value is calculated from the memory data T within each cycle in horizontal and vertical direction of the latticed patterns (shown in FIG. 5A). The average values are temporally memorized in the RAM as memorized data Tb.

Hereafter, the process at step 136 will be described in detail. A process at step 133 through 135a is effective to detect the defect as shown in FIG. 5B. In FIG. 5B, a part of the latticed patterns is deformed. Therefore the defect signal of a high frequency component and a low frequency component is generated on both sides of the deformed lattice. That is, the variance value tends to increase in the local variance process because the amplitude of the image data is increased by the defect signal of the high frequency component and the low frequency component. However, in a case of a lack of a part of the lattice or a case that an abnormal lattice is additionally formed among the normal lattices, only one of the high frequency component or the low frequency component is generated. Therefore, it is difficult to detect the defect by the above-mentioned process.

At step 136, averages of a signal amplitude of the image data at each cycle of the latticed patterns are calculated for detecting the defect. It is effective for the case of a lack of a part of the lattice or the case that an abnormal lattice is additionally formed among the normal lattices. In the case of a lack of a part of the lattice, the average value decreases abnormally. In the case that an abnormal lattice is additionally formed among the normal lattices, the average value increases abnormally. The data processed by the averaging process is binarized at step 136. The binarized data is memorized in the RAM as the memory data Tb.

At step 137, a masking process of a non-examining area is carried out. For instance, the memorized data Tf in step 135a and the examining area data R are multiplied, and a result is placed as the data Tf. The memorized data Tb in step 136a and the examining area data R are multiplied, and a result is placed as memorized data. Then, the masking process is finished.

At step 138, a labeling process is carried out to both of the data Tf and Tb. In this labeling process, a display data is obtained on a position of the proposed defect for providing a display based on both of the binary data Tf and Tb. Finally, at step 139, a position of the proposed defect of the latticed patterns on the surface of the object S is displayed on the CRT 80 based on the result of the labeling process.

At step 140, it is discriminated that whether the proposed defect exists on the latticed patterns of the surface of the object S or not based on the result of the defect detecting routine 130, when the defect detecting routine 130 is finished. In a case that there is no proposed defect, the program branches to NO from step 140, at step 161, the object S is determined as a good product.

On the contrary, in a case of YES from step 140, at step 141, the motor 13 and 14 drive the X-table 11 and the Y-table 12 to a position (referred to as a high magnification station or a second station) where the surface on the object S is located within the field of the high magnification camera 30. The object S is positioned on the low magnification station. After that, the high magnification camera 30 captures an image of the surface of the object S at high magnification when the light 50 lights up the surface of the object S. The high magnification camera 30 outputs captured data to the A-D converter 60. The A-D converter 60 converts the captured data from the high magnification camera 30 digitally and outputs it to the microcomputer 70 as high magnification captured data. At step 142, the microcomputer 70 inputs the high magnification captured data (second data).

At step 143, the high magnification data is binarized. At step 144, the labeling process is carried out to the binarized data. In this binarizing process, each area enclosed by the lattice in the position of the proposed defect is determined.

After that, at step 145, a central point of each determined area enclosed by the lattice is calculated. That is, a central point of the area enclosed by the lattice is used as a parameter for evaluating a shape of the lattice. At step 150, it is discriminated whether it is a normal or an abnormal based on whether the calculated central point is positioned in a permissible range indicating a normal lattice or not. In a case that the proposed defect still remains, the process after step 141 is repeatedly executed under a decision of NO at step 160.

When the decision of step 160 turns into YES, the object S is determined as a good product. On the contrary, in a case of NO at step 150, the object S is determined as a bad product.

In this embodiment, the apparatus determines the position of the proposed defect based on the low magnification image of the surface of the object S, and determines whither the object S is a good or a bad based on the high magnification image of the area containing the position of the proposed defect of the surface. Here, it is possible to detect a lot of the proposed defect from one image, because the low magnification image of the object S covers a wide area of the surface. Accordingly, number of images are decreased relative to a case that the proposed defect is determined based on the high magnification image having a narrower area of the surface of the object S. In other words, the proposed defect of the result of the low magnification examining is merely examined by the high magnification. The number of the images required for determining whether the object S is a good or not is extremely decreased. It is possible to examine the object S with the same examining accuracy without a large capacity of the memory. Accordingly, it is possible to improve the examining accuracy of a quality of the object S and to shorten a processing time required for examining the quality of the object S.

FIG. 6 shows a second embodiment. An industrial robot 200 is adopted in place of the XY-table 10 of the first embodiment. The industrial robot 200 is located by the object S mounted on an appropriate mounting jig. The industrial robot 200 operates the robot hand 201 along the X-axis, Y-axis and Z-axis. The industrial robot 200 holds the camera 210 with a zoom mechanism by the robot hand 201. The industrial robot 200 operates the robot hand 201 so that the camera 210 captures the surface of the object S by low magnification or high magnification. The other constructions are equivalent to the first embodiment.

The industrial robot 200 operates the camera 210 to a position corresponding to the low magnification station relative to the surface of the object S when the computer program proceeds to step 110 of FIG. 2. The camera 210 captures the surface of the object S by the low magnification and outputs the captured data to the A-D converter 60. At step 120, the microcomputer 70 inputs the low magnification data converted by the A-D converter 60. After that, the defect detecting routine 130 is carried out based on the low magnification data similarly to the first embodiment.

The industrial robot 200 operates the camera 210 to a position corresponding to the high magnification station relative to the surface of the object S when the computer program proceeds to step 140 of FIG. 3. The camera 210 captures the surface of the object S by the high magnification and outputs the captured data to the A-D converter 60. At step 142, the microcomputer 70 inputs the high magnification data converted by the A-D converter 60. After that, the process after step 143 is carried out based on the high magnification data and the result of the defect detecting routine 130 similarly to the first embodiment.

The industrial robot 200 and the camera with a zoom mechanism can provide function and effect similar to the first embodiment. In this case, the examining apparatus is simplified because only one camera 210 is used.

Although the present invention has been fully described in connection with preferred embodiments thereof with reference to the accompanying drawings, it is to be noted that various changes and modifications will become apparent to those skilled in the art. Such changes and modifications are to be understood as being within the scope of the present invention as defined by the appended claims.

What is claimed is:

1. An apparatus for examining a defect of a monolithic substrate used as a catalyst for purifying engine exhaust, the monolithic substrate having an outer edge forming a predetermined shape and regularly latticed patterns enclosed by the outer edge, the apparatus comprising:

means for capturing a surface of said monolithic substrate including the outer edge and the latticed patterns enclosed by the outer edge and for outputting image data;

means for transforming said image data into space frequency data by using a Fourier transformation;

means for processing said space frequency data to provide frequency data in which a frequency component corresponding to said outer edge and said latticed patterns are declined by removing frequency data contained within circular ranges which have centers corresponding to a plurality of frequency components of said latticed patterns and a predetermined area;

means for restoring image data from said frequency data provided by said processing means by using a Fourier reverse transformation; and means for detecting an existence of a defect of said latticed patterns on said surface of said monolithic substrate based on said restored image data.

2. An apparatus for examining a defect of a monolithic substrate according to claim 1, further comprising:

means for capturing an image by a high magnification higher than said capturing means;

means for determining whether said defect detected in said detecting means is permissible or not based on high magnification image data of an area around said defect, said high magnification image data being captured by said high magnification capturing means when said detecting means detects an existence of said defect; and means for taking said monolithic substrate as a bad product when said determining means determines said defect is not permissible.

3. An apparatus for examining a defect of a monolithic substrate according to claim 1, further comprising:

means for processing said restored image data by dividing said restored image data into a plurality of area, obtaining signal variances in said areas and emphasizing a signal amplitude of said area having a relative large variance, wherein said detecting means detects an existence of a defect of said latticed patterns on said surface of said monolithic substrate based on said emphasized image data.

4. An apparatus for examining a defect of a monolithic substrate according to claim 2, further comprising:

means for processing said restored image data by dividing said restored image data into a plurality of area, obtaining signal variances in said areas and emphasizing a signal amplitude of said area having a relative large variance, wherein said detecting means detects an existence of a defect of said latticed patterns on said surface of said monolithic substrate based on said emphasized image data.

5. An apparatus for examining a defect of a monolithic substrate used as a catalyst for purifying engine exhaust, the monolithic substrate having an outer edge forming a predetermined shape and regularly latticed patterns enclosed by the outer edge, the apparatus comprising:

means for capturing a surface of said monolithic substrate including the outer edge and the latticed patterns enclosed by the outer edge and outputting image data;

means for calculating an average of said image data in a lattice corresponding to a cycle of said latticed patterns;

means for detecting a defect of said latticed patterns on said surface of said monolithic substrate when said average is not permissible.

6. An apparatus for examining a defect of a monolithic substrate according to claim 5, further comprising:

means for capturing an image by a high magnification higher than said capturing means;

means for determining whether said defect detected in said detecting means is permissible or not based on high magnification image data of an area around said defect, said high magnification image data being captured by said high magnification capturing means when said detecting means detects an existence of said defect; and means for taking said monolithic substrate as a bad product when said determining means determines said defect is not permissible.

7. A method for examining a defect of a monolithic substrate used as a catalyst for purifying engine exhaust, the monolithic substrate having an outer edge forming a predetermined shape and regularly latticed patterns enclosed by the outer edge, the method comprising:

capturing a surface of said monolithic substrate including the outer edge and the latticed patterns enclosed by the outer edge;

outputting captured image data;

transforming said image data into space frequency data by using a Fourier transformation;

processing said space frequency data to provide frequency data in which frequency components corresponding to said outer edge and said latticed patterns are declined by removing frequency data contained within circular ranges which have centers corresponding to a plurality of frequency components of said latticed patterns and a predetermined area;

restoring image data from said frequency data provided by said processing step by using a Fourier reverse transformation; and detecting an existence of a defect of said latticed patterns on said surface of said monolithic substrate based on said restored image data.

8. A method for examining a defect of a monolithic substrate, according to claim 7, further comprising:

capturing image data of an area around said defect as high magnification image data having higher magnification than said captured image data when said defect is detected;

determining whether said defect is permissible or not based on high magnification image data; and taking said monolithic substrate as a bad product when said defect is not permissible.

9. A method for examining a defect of a monolithic substrate, according to claim 7, further comprising:

processing said restored image data by dividing said restored image data into a plurality of area, obtaining signal variances in said areas and emphasizing a signal amplitude of said area having a relative large variance, wherein an existence of a defect of said latticed patterns on said surface of said monolithic substrate is detected on the basis of said emphasized image data.

10. A method for examining a defect of a monolithic substrate, according to claim 8, further comprising:

processing said restored image data by dividing said restored image data into a plurality of area, obtaining signal variances in said areas and emphasizing a signal amplitude of said area having a relative large variance, wherein an existence of a defect of said latticed patterns on said surface of said monolithic substrate is detected on the basis of said emphasized image data.

11. A method for examining a defect of a monolithic substrate used as a catalyst for purifying engine exhaust, the monolithic substrate having an outer edge forming a predetermined shape and regularly latticed patterns enclosed by the outer edge, the method comprising:

capturing a surface of said monolithic substrate including the outer edge and the latticed patterns enclosed by the outer edge;

outputting captured image data;

calculating an average of said image data in a lattice corresponding to a cycle of said latticed patterns; and detecting a defect of said latticed patterns on said surface of said monolithic substrate when said average is not permissible.

12. A method for examining a defect of a monolithic substrate, according to claim 11, further comprising:

capturing image data of an area around said defect as high magnification image data having higher magnification than said captured image data when said defect is detected;

determining whether said defect is permissible or not based on high magnification image data; and taking said monolithic substrate as a bad product when said defect is not permissible.

13. An apparatus for examining a defect of a monolithic substrate according to claim 1, wherein said plurality of frequency components of said latticed patterns include low frequency components.

14. An apparatus for examining a defect of a monolithic substrate according to claim 13, wherein said low frequency components include zero and first degree components.

15. An apparatus for examining a defect of a monolithic substrate according to claim 2, wherein said high magnification capturing means captures a new image of said monolithic substrate.

16. An apparatus for examining a defect of a monolithic substrate according to claim 15, wherein said high magnification capturing means captures a partial image of said monolithic substrate including said defect of said latticed patterns detected by said detecting means.

* * * * *